United States Patent
Plassat et al.

(10) Patent No.: US 11,185,589 B2
(45) Date of Patent: Nov. 30, 2021

(54) FORMULATION FOR ORAL DELIVERY OF PROTEINS, PEPTIDES AND SMALL MOLECULES WITH POOR PERMEABILITY

(71) Applicant: R.P. Scherer Technologies, LLC, Carson City, NV (US)

(72) Inventors: Vincent Plassat, La Ferté Alais (FR); Benoit Hilbold, Schiltigheim (FR); Aurélia Galus, Weyersheim (FR); Thomas Pointeaux, Reichstett (FR); Julien Meissonnier, Souffelweyersheim (FR)

(73) Assignee: R.P. Scherer Technologies, LLC, Carson City, NV (US)

( * ) Notice: Subject to any disclaimer, the term of this patent is extended or adjusted under 35 U.S.C. 154(b) by 0 days.

(21) Appl. No.: 16/845,830

(22) Filed: Apr. 10, 2020

(65) Prior Publication Data
US 2020/0323985 A1 Oct. 15, 2020

Related U.S. Application Data

(60) Provisional application No. 62/832,508, filed on Apr. 11, 2019.

(51) Int. Cl.
*A61K 47/14* (2017.01)
*A61K 38/03* (2006.01)
*A61K 47/34* (2017.01)

(52) U.S. Cl.
CPC .............. *A61K 47/14* (2013.01); *A61K 38/03* (2013.01); *A61K 47/34* (2013.01)

(58) Field of Classification Search
CPC ........ A61K 38/00; A61K 47/14; A61K 47/34; A61K 9/10
See application file for complete search history.

(56) References Cited

U.S. PATENT DOCUMENTS

| | | | |
|---|---|---|---|
| 6,096,338 A * | 8/2000 | Lacy | A61K 9/4858 424/451 |
| 8,323,695 B2 | 12/2012 | Huang et al. | |
| 8,859,623 B1 | 10/2014 | Witham et al. | |
| 9,259,389 B2 * | 2/2016 | Meissonnier | A61P 9/00 |
| 9,308,166 B2 | 4/2016 | Agisim et al. | |
| 2005/0079145 A1 | 4/2005 | Constantinides et al. | |
| 2005/0249802 A1 | 11/2005 | Khanolkar et al. | |
| 2007/0298099 A1 | 12/2007 | Peresypkin et al. | |
| 2008/0014274 A1 | 1/2008 | Bubnis et al. | |
| 2008/0260840 A1 * | 10/2008 | Alessi | A61K 47/20 424/489 |
| 2010/0210568 A1 * | 8/2010 | Bevec | A61P 25/18 514/6.9 |
| 2012/0316132 A1 * | 12/2012 | Meissonnier | A61P 9/00 514/56 |
| 2013/0309226 A1 * | 11/2013 | Armstrong | A61K 39/39541 424/133.1 |
| 2015/0147399 A1 * | 5/2015 | Vol | A61K 9/0053 424/178.1 |
| 2017/0037117 A1 | 2/2017 | Dillin et al. | |
| 2017/0100355 A1 | 4/2017 | Cavatur et al. | |

FOREIGN PATENT DOCUMENTS

| | | | |
|---|---|---|---|
| CA | 2439366 A1 | 9/2002 | |
| GB | 2228198 A | 8/1990 | |
| WO | WO-2017093810 A2 * | 6/2017 | ............. A61K 47/14 |

OTHER PUBLICATIONS

Aungst (AAPS Journal, 2012, vol. 14, pp. 10-18) (Year: 2012).*
Amidon et al. (Mar. 1995). "A Theoretical Basis for a Biopharmaceutic Drug Classification: The Correlation of in Vitro Drug Product Dissolution and in Vivo Bioavailability," Pharmaceutical Research 12(3):413-420.
Lyons et al. (Jan. 2000). "Factors limiting the oral bioavailability of N-acetylglucosaminyl-N-acetylmuramyl dipeptide (GMDP) and enhancement of absorption in rats by delivery in a water-in-oil microemulsion," International Journal of Pharmaceutics 199:17-28.
International Search Report and Written Opinion dated Jul. 22, 2020, directed to International Application No. PCT/US2020/027800; 14 pages.
International Search Report and Written Opinion dated Jul. 22, 2020, directed to International Application No. PCT/US2020/027801; 14 pages.
Tepper. (Mar. 5, 2019). "CGRP and headache: a brief review," Neurological Sciences 40(1): S99-S105.

* cited by examiner

*Primary Examiner* — Mark V Stevens
(74) *Attorney, Agent, or Firm* — Morrison & Foerster LLP

(57) ABSTRACT

The present disclosure is directed to a pharmaceutical formulation intended for oral delivery of synthetic or natural poorly permeable molecules or salts/solvates thereof having a therapeutic activity. The pharmaceutical formulation can include a synthetic or natural poorly permeable molecule or salt or solvate thereof in an amount 0.01-10 wt. % of the total weight of the formulation; a lipophilic phase comprising triglycerides of fatty acids in an amount of 50-80 wt. % of the total weight of the formulation; and at least one lipophilic surfactant comprising partial esters of polyol and fatty acids in an amount of about 10-50 wt. % of the total weight of the formulation.

14 Claims, No Drawings

FORMULATION FOR ORAL DELIVERY OF PROTEINS, PEPTIDES AND SMALL MOLECULES WITH POOR PERMEABILITY

CROSS-REFERENCE TO RELATED APPLICATIONS

This application claims the priority of U.S. Provisional Application No. 62/832,508, filed Apr. 11, 2019, the entire contents of which are incorporated herein by reference.

FIELD OF THE DISCLOSURE

This disclosure relates to a formulation for oral delivery of proteins, peptides and small molecules with poor permeability. More specifically, this disclosure relates to a pharmaceutical formulation intended for oral delivery of any molecule synthetic or natural with poor permeability or salts or solvates thereof having a therapeutic activity.

BACKGROUND OF THE DISCLOSURE

Poorly permeable molecules are compounds that have poor absorption through the intestinal membrane. As such, they are administered intravenously or subcutaneously. Because of their poor absorption through the intestinal membrane, their clinical use is considerably restricted given the need to be administered IV and dosed several times a day (e.g., insulin for diabetics). These poorly permeable compounds are identified as BCS class III and class IV compounds in the classification proposed by Amidon GL in *A theoretical basis for a biopharmaceutic drug classification: the correlation of in vitro drug product dissolution and in vivo bioavailability* (Pharm Res. 1995 March; 12(3):413-20.), which is hereby incorporated by reference in its entirety.

SUMMARY OF THE DISCLOSURE

Applicants have developed formulations for orally administered molecules with poor permeability. These formulations are highly beneficial for patients that require dosing several times a day. In order to prepare such formulations for oral delivery of poorly permeable molecules, Applicants had to overcome at least this poor permeability against the intestinal membrane; and for some of those molecules in particular peptides and proteins the chemical and physical instability in the gastrointestinal tract and specifically, the loss of activity due to acidic conditions in the stomach; and enzymatic degradation throughout the intestine. Accordingly, Applicants developed delayed release coated dosage form that can deliver poorly permeable molecules in the intestine with in-situ production of permeation enhancer to increase its bioavailability.

In U.S. Pat. No. 9,259,389, the inventors found that a digestible reverse emulsion can increase bioavailability of oligosaccharides. Unexpectedly, Applicants found that a solution of lipid excipients with a poorly permeable molecule dispersed as a powder in the formulation can allow better results of bioavailability for this specific class of molecules (i.e., BCS Class III and Class IV compounds in the classification proposed by Amidon GL et al(Pharm Res. 1995 March; 12(3):413-20.)). Specifically, Applicants found that for poorly permeable molecules, specifically BCS Class III protein and peptide compounds, the formulation without addition of water can be beneficial. Without being bound by any theory, it is believed that water tends to cause this class of the poorly permeable molecules to aggregate together. More particularly, Applicants found that when they did not include water in the formulation comprising a solution of lipid based excipients with the poorly permeable BCS Class III protein or peptide molecule or salt dispersed as a powder in the formulation, higher results of bioavailability were achieved for this specific class of molecules. In contrast, the removal of water was detrimental for saccharides of U.S. Pat. No. 9,259,389.

In addition, Applicants can increase the drug load when the API can be dispersed as a powder without the need to solubilize the active pharmaceutical ingredient ("API") in water given there is no need to solubilize the API. Furthermore, the formulation is inherently more physically stable because lipid excipients can be in solution as a single phase. Thus, there may be no need to add a stabilizing agent such as silicon dioxide to stabilize the phases. In some embodiments, a thickener may be added for manufacturing purposes to maintain homogeneity of the API powder in suspension during the process. In some embodiments, the thickener can be silicon dioxide. Lastly, compared to other formulations found in literature using excipients such as permeation enhancers, the formulations disclosed herein can use only generally recognized as safe excipients or already marketed ingredients.

In some embodiments, a pharmaceutical formulation comprising a synthetic or natural poorly permeable molecule or salt or solvate thereof in an amount 0.01-20 wt. % of the total weight of the formulation; a lipophilic phase comprising triglycerides of fatty acids in an amount of 50-80 wt. % of the total weight of the formulation; and at least one lipophilic surfactant comprising partial esters of polyol and fatty acids in an amount of 10-50 wt. % of the total weight of the formulation. In some embodiments, the synthetic or natural poorly permeable molecule or salt or solvate thereof is a BCS Class III or Class IV compound. In some embodiments, the synthetic or natural poorly permeable molecule is a peptide or protein. In some embodiments, the peptide has from 5 to 20 amino acids. In some embodiments, the formulation comprises at least one hydrophilic surfactant with a hydrophilic lipophilic balance ("HLB") above 10 in an amount of 1-30 wt. % of the total weight of the formulation. In some embodiments, the at least one hydrophilic surfactant is selected from the group consisting of polyoxyethylene (20) monooleate, PEG 8 caprylic/capric glycerides, PEG 6 caprylic/capric glycerides, poly(oxyethylene)(4)Lauryl ether and mixtures thereof. In some embodiments, the triglycerides of fatty acids are medium chain fatty acids. In some embodiments, the lipophilic surfactant comprises a mixture of mono and diglyceride of medium chain fatty acids. In some embodiments, the formulation does not include water. In some embodiments, a delayed release pharmaceutical dosage form comprises any of the formulations described above, wherein the delayed release dosage form is a coated dosage form whose release is pH dependent. In some embodiments, a method for treating a patient comprises administering to a person in need thereof an effective amount of any of the formulations described above.

Additional advantages will be readily apparent to those skilled in the art from the following detailed description. The examples and descriptions herein are to be regarded as illustrative in nature and not restrictive.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

DETAILED DESCRIPTION OF THE DISCLOSURE

The present disclosure concerns pharmaceutical formulations intended for oral administration containing synthetic or natural poorly permeable molecules and having a therapeutic activity or a pharmaceutically acceptable additions salt or solvate thereof. These formulations can be a lipid based formulation. In addition, these formulations can be a delayed release dosage form. In some embodiments, the dosage form can be a delayed release softgel capsule, a hard-shell capsule or a combination of thereof. In some embodiments this delayed release dosage form can be an enteric released dosage form.

The formulations can include: (A) synthetic or natural poorly permeable molecules; (B) a lipophilic phase; (C) at least one lipophilic surfactant; and/or (D) at least one hydrophilic surfactant. In some embodiments, the formulations can include a chemical and/or physical stabilization agent.

Synthetic or Natural Poorly Permeable Molecules

In some embodiments, the formulation can include synthetic or natural poorly permeable molecules or any pharmaceutically acceptable salts of these poorly permeable molecules in an amount up to about 1 wt. %, about 2 wt. %, about 5 wt. %, about 10 wt. %, about 15.%, or about 20 wt. % of the total weight of the formulation. In some embodiments, the formulation can include synthetic or natural poorly permeable molecules or any pharmaceutically acceptable salts of these poorly permeable molecules in an amount of about 0.01-30 wt. %, about 0.1-30 wt. %, about 0.01-20 wt. %, about 0.1-20 wt. %, about 0.1-15 wt. %, about 0.1-10 wt. %, about 0.1-5 wt. %, about 0.1-2 wt. %, about 0.1-1 wt. %, about 0.1-0.5 wt. %, or about 0.5-1.5 wt. % of the total weight of the formulation.

The synthetic or natural poorly permeable molecule or pharmaceutically acceptable salts thereof can include: any protein, polypeptide, peptide, or small molecule with poor permeability intended for oral delivery wherein the active component according to the invention can be, but not limited to, insulin, human growth hormone, calcitonin (e.g., salmon calcitonin), an interferon such as an α-, β-, or γ-interferon, glucagon, gonadotropin-releasing hormone, enkephalins, vaccines, enzymes, hormone analogs, enzyme inhibitors, antibody and antibody mimetics. The synthetic or natural poorly permeable molecule or pharmaceutically acceptable salts thereof are those identified as BCS Class III and Class IV in the classification proposed by Amidon G L in *A theoretical basis for a biopharmaceutic drug classification: the correlation of in vitro drug product dissolution and in vivo bioavailability* (Pharm Res. 1995 March; 12(3):413-20.)

Lipophilic Phase

In some embodiments, the formulation can include a lipophilic phase in an amount of up to about 50 wt. %, about 55 wt. %, about 60 wt. %, about 65 wt. %, about 70 wt. %, or about 80 wt. % of the total weight of the formulation. In some embodiments, the formulation can include a lipophilic phase in an amount of about 50-80 wt. %, about 55-75 wt. %, about 60-70 wt. %, about 62-68 wt. %, about 64-66 wt. %, or about 65 wt. % of the total weight of the formulation.

In some embodiments, the lipophilic phase can be triglycerides of fatty acids. Triglycerides of fatty acids can mean any triglycerides of saturated or unsaturated fatty acid which are pharmaceutically and orally acceptable. In some embodiments, the triglycerides of fatty acid can have the following formula:

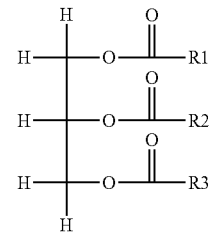

in which R1, R2, and R3 represent independently of each other the alkyl or alkenyl group of the parent fatty acid.

The fatty acid can be saturated or unsaturated. In particular, the fatty acid can be saturated since unsaturated fatty acid can give slower digestion kinetic and lower digestion percentages. Some common saturated fatty acids are indicated in the following Table 1.

TABLE 1

| Common name | IUPAC name | Chemical structure | Abbr. | Melting point (° C.) |
|---|---|---|---|---|
| Butyric | Butanoic acid | $CH_3(CH_2)_2COOH$ | C4:0 | −8 |
| Caproic | Hexanoic acid | $CH_3(CH_2)_4COOH$ | C6:0 | −3 |
| Caprylic | Octanoic acid | $CH_3(CH_2)_6COOH$ | C8:0 | 16-17 |
| Capric | Decanoic acid | $CH_3(CH_2)_8COOH$ | C10:0 | 31 |
| Lauric | Dodecanoic acid | $CH_3(CH_2)_{10}COOH$ | C12:0 | 44-46 |
| Mystiric | Tetradecanoic acid | $CH_3(CH_2)_{12}COOH$ | C14:0 | 58.8 |
| Palmitic | Hexadecanoic acid | $CH_3(CH_2)_{14}COOH$ | C16:0 | 63-64 |
| Stearic | Octadecanoic acid | $CH_3(CH_2)_{16}COOH$ | C18:0 | 69.9 |
| Arachidic | Eicosanoic acid | $CH_3(CH_2)_{18}COOH$ | C20:0 | 75.5 |
| Behenic | Docosanoic acid | $CH_3(CH_2)_{20}COOH$ | C22:0 | 74-78 |
| Lignoceric | Tetracosanoic acid | $CH_3(CH_2)_{22}COOH$ | C24:0 | |

R1, R2, and R3 can represent a straight or branched chain. In some embodiments, R1, R2, and R3 can be $C_3$-$C_{23}$ alkyl or alkenyl groups, $C_5$-$C_{13}$ alkyl or alkenyl groups, or $C_7$-$C_9$ alkyl or alkenyl groups. In some embodiments, fatty acids are saturated fatty acids and are medium chain fatty acids. As such, the lipophilic phase can be triglycerides of long, (such as for example soya bean oil and fish oil), medium or short (such as for example glyceryl triacetate) chain fatty acids. In some embodiments, the triglycerides can be of caprylic acid, capric acid, or mixtures thereof (such as for example the commercial product Miglyol 812®, Captex 355®, Estasan®, Neobee M5®, Labrafac CC®, and Captex 1000®). In some embodiments, the triglycerides can be triglycerides of $C_6$-$C_{12}$ fatty acids or $C_5$-$C_{10}$ fatty acids.

Lipophilic Surfactant

In some embodiments, the formulation can include at least one lipophilic surfactant in an amount of up to about 1 wt. %, about 5 wt. %, about 10 wt. %, about 15 wt. %, about 20 wt. %, about 25 wt. %, about 30 wt. %, about 35 wt. %, about 40 wt. %, about 45 wt. %, or about 50 wt. % of the total weight of the formulation. In some embodiments, the formulation can include at least one lipophilic surfactant in an amount of about 10-50 wt. %, about 15-35 wt. %, about 20-30 wt. %, about 22-28 wt. %, about 24-26 wt. %, or about 25 wt. % of the total weight of the formulation. If the formulation includes less than about 10 wt. % of the at least one lipophilic surfactant the kinetic digestion may not be optimized. If the formulation includes more than 50 wt. % of at least one lipophilic surfactant, the amount of lipophilic phase available for release of sodium caprate may not be optimal.

In some embodiments, the at least one lipophilic surfactant can be partial esters of polyol and fatty acids. Partial esters of polyol and fatty acids can mean any partial esters obtained by esterification of polyols and saturated or unsaturated fatty acids which are pharmaceutically and orally acceptable. Common saturated fatty acids are indicated in the above-mentioned Table 1. The fatty acids can be medium chain fatty acids, such as $C_6$-$C_2$ fatty acids, in particular caprylic and/or capric acid. The polyols can be for example propylene glycol and glycerol. For example, the partial esters of polyol and fatty acids can be propylene glycol mono- and/or di-esters of fatty acids (such as the propylene glycol monolaurate sold under the trade name Lauroglycol®, the propylene glycol monomyristate sold under the trade name Mirpyl® or the propylene glycol dicaprylate/dicaprate sold under the trade name Captex 200®, Miglyol 840®, or Neobee M-20®) and/or polyglycerol esters of fatty acids (such as the polyglyceryl oleate sold under the trade name Plurol Oleique® or Drewpol 10.10.1 or the polyglyceryl mixed fatty acids sold under the trade name Caprol ET®).

The at least one lipophilic surfactant can be partial esters of propylene glycol and fatty acids (such as for example the commercial product Capryol PGMC® and Capmul PG-8®). In some embodiments, the at least one lipophilic surfactant can be a mixture of mono and diglyceride of fatty acids, a mixture of mono and diglyceride of medium chain fatty acids, a mixture of mono and diglyceride of caprylic and/or capric acid (such as for example the commercial product Capmul MCM and Capmul MCM C8®, Imwitor 988®, Imwitor 742®), or a mixture of mono and diglyceride of capric acid (such as for example the commercial product Capmul MCM C100 or Imwitor 308®).

In some embodiments, the at least one lipophilic surfactant can be a lecithin, e.g., soybean lecithin, as but not limited to soybean lecithin.

Hydrophilic Surfactant

In some embodiments, the formulation can include at least one hydrophilic surfactant in an amount of up to about 2 wt. %, about 5 wt. %, about 8 wt. %, about 10 wt. %, about 15 wt. %, about 20 wt. %, about 25 wt. %, or about 30 wt. % of the total weight of the formulation. In some embodiments, the formulation can include at least one hydrophilic surfactant in an amount of about 0-30 wt. %, about 0-15 wt. %, about 0-10 wt. %, about 1-30 wt. %, about 5-15 wt. %, about 8-12 wt. %, about 9-11 wt. %, or about 10 wt. % of the total weight of the formulation. If the amount of the at least one hydrophilic surfactant is greater than about 30 wt. % of the formulation, the amount of lipophilic phase available for release of sodium caprate could be compromised.

In some embodiments, the at least one hydrophilic surfactant can be any hydrophilic surfactant having a hydrophilic lipophilic balance ("HLB") value above 10 which are pharmaceutically and orally acceptable. The HLB value is an empirical parameter commonly used by one skilled in the art to characterize the relative hydrophilicity and hydrophobicity of a non-ionic surfactant.

In some embodiments, the at least one hydrophilic surfactant can be phospholipids; polyoxyethylene sorbitan fatty acids derivatives, such as polyoxyethylene (20) monolaurate (sold under the trade name Tween 20®), polyoxyethylene (20) monooleate (sold under the trade name Tween 80® and/or Crillet 4®) or the polyoxyethylene (20) monopalmitate (sold under the trade name Montanox 40®); castor oil or hydrogenated castor oil ethoxylates with a HLB value above 10, such as polyoxyethylene (35) castor oil (sold under the trade name Cremophor EL®), polyoxyethylene (40) hydrogenated castor oil (sold under the trade name Cremophor RH40®), polyoxyethylene (40) castor oil (sold under the trade name Etocas 40®) or polyoxyethylene (60) hydrogenated castor oil (sold under the trade name Nikkol HCO-60®); fatty acids ethoxylates with a HLB value above 10, such as polyoxyethylene (8) stearate (sold under the trade name Myrj 45®), polyoxyethylene (30) monolaurate (sold under the trade name Tagat L®), polyoxyethylene (20) stearate (sold under the trade name Marlosol 1820®) or polyoxyethylene (15) oleate (sold under the trade name Marlosol OL15®), alcohol ethoxylates with a 1LB value above 10, such as polyoxyethylene (10) oleyl ether (sold under the trade name Brij 96®), polyoxyethylene (15) oleyl ether (sold under the trade name Volpo 015®), polyoxyethylene (30) oleyl ether (sold under the trade name Marlowet OA30®) or polyoxyethylene (20) $C_{12}$-$C_{14}$ fatty ether (sold under the trade name Marlowet IMA20®); polyoxvethylene-polyoxypropylene co-polymers and block co-polymers with a HLB value above 10, such as the products sold under the trade name Syperonic PE L44® with a HLB value=16 or the products sold under the trade name Syperonic F127® with a 1LB value=22; anionic surfactants, such as the sodium lauryl sulphate, the sodium oleate or the sodium dioctylsulphosuccinate or alkylphenol surfactants with a HLB value above 10, such as the polyoxyethylene (9-10) nonylphenol (sold under the trade name Triton N-101®) or the polvoxyethvlene (9) nonylphenol (sold under the trade name Synperonic NP9®); Vitamin E; D-alpha-tocopheryl Polyethyelene glycol Succinate (TPGS); or PEG 15 Hydroxystearate (sold under the trade name Solutol HS15®).

In some embodiments, the at least one hydrophilic surfactant is a polyethoxylated surfactant. In some embodiments, the at least one hydrophilic surfactant is chosen from the group consisting of polyoxyethylene sorbitan fatty acid esters, polyoxyethylene alkyl ethers, and polyoxyethylene esters of fatty acids such as polyoxyethylene esters of glycerol and fatty acids. In some embodiments, the fatty acids are saturated or unsaturated. Common saturated fatty acids are indicated in the above-mentioned Table 1. In some embodiments, the fatty acids are medium chain fatty acids, such as $C_6$-$C_{12}$ fatty acids (e.g., lauric, caprylic, and/or capric acid).

In some embodiments, the number of ethylene oxide group units in the surfactant can be between 4 and 20. In some embodiments, the at least one hydrophilic surfactant can be chosen from the group consisting of polyoxyethylene (20) monooleate (such as for example the commercial product Tween 80®), PEG 8 caprylic/capric glycerides (such as for example the commercial product Labrasol®), PEG 6 caprylic/capric glycerides (such as for example the commercial product Softigel 767®), poly(oxyethylene(4) Lauryl ether (such as for example the commercial product Brij 30®) and mixtures thereof.

Hydrophilic Solvent

In some embodiments, the formulation can include at least one anhydrous hydrophilic solvent in an amount of up to about 15 wt. %, about 10 wt. %, about 5 wt. %, or about 1 wt. % of the total weight of the formulation to aid in solubilizing the API. In some embodiments, the formulation is free from at least one hydrophilic solvent. In some embodiments, at least one hydrophilic solvent is added, for example, to solubilize the thickener.

In some embodiments, the at least one hydrophilic solvent can be chosen from the group consisting of propylene glycol, PEG 400 diethylene glycol monoethyl ether, glycerol triacetate, ethanol, glycerol, dimethylisosorbide, N-methyl-2-pyrrolidone, poloxamers, and mixtures thereof.

Chemical and/or Physical Stabilization Agent

In some embodiments, the formulation can include at least one chemical and/or physical stabilization agent in an amount of up to about 25 wt. % of the total weight of the formulation. In some embodiments, the physical stabilization agent may be added to maintain uniformity of the API powder suspension during processing. As discussed below, the placebo formulation is physically stable given it is a single phase consisting of lipid excipients in solution, but since the API powder is dispersed as a suspension, to maintain the homogeneity, a thickener is added.

The chemical and/or physical stabilization agent can be any pharmaceutical ingredient which will improve the poorly permeable molecule chemical stability in the formulation in order to comply with the ICH Harmonized Tripartite Guideline ICH Q3B (Impurities in new drug products) requirements Current step 4 version dated Jun. 2, 2006 or which will improve the poorly permeable molecule formulation physical stability.

In some embodiments, a chemical stabilization agent can be a lipophilic surfactant. For example, the chemical stabilization agent can be acetic, succinic, lactic, citric and/or tartaric esters of mono- and/or di-glycerides of fatty acids such as distilled acetylated monoglycerides (sold under the trade name Myvacet 945®), caprylic/capric diglyceryl succinate (sold under the trade name Miglyol 829®), mono/di-succinylated monoglycerides (sold under the trade name Myverol SMG®), glyceryl stearate citrate (sold under the trade name Imwitor 370®), glyceryl monostearate/citrate/lactate (sold under the trade name Imwitor 375®) or diacetyl tartaric asters of monoglycerides (sold under the trade name Cordatem T22®); acid ester ethoxylates formed by reacting ethylene oxide with fatty acids or glycerol esters of fatty acids with a HLB value below 10, such as polyoxyethylene (4) lauric acid (sold under the trade name Crodet 04®), polyoxyethylene (2) stearic acid (sold under the trade name Cithrol 2MS®), polyoxyethylene (3) stearic acid (sold under the trade name Marlosol 183®) or glyceryl 12 EO dioleate (sold under the trade name Marlowet G12DO®); sorbitan esters of fatty acids, such as sorbitan monolaurate (sold under the trade name Span 20® or Crill 1®) or sorbitan mono-oleate (sold under the trade name Crill 4®); transesterification products of natural or hydrogenated vegetable oil triglyceride and polyalkylene polyol with a HLB value below 10 such as polyoxyethylated apricot kernal oil (sold under the trade name Labrafil M1944CS®), polyoxyethylated corn oil (sold under the trade name Labrafil M2125CS®) or polyoxyethylated hydrogenated oil (sold under the trade name Gelucire 37/06®); or alcohol ethyoxylates with a HLB value below 10 such as polyoxyethylated (3) oleyl ether (sold under the trade name Volpo N3®), polyoxyethylated (2) oleyl ether (sold under the trade name Brij 93®) or polyoxyethylated (4) lauryl ether (sold under the trade name Marlowet LA4®).

In some embodiments, a chemical stabilization agent can be buffering agents such as citrate, phosphate, or acetate buffers and/or thickening agents such as partially hydrogenated oils, hydrogenated oils, or monoesters of unsaturated or saturated fatty acids, polyvinylpyrrolidone derivative, polyethylene oxide.

In some embodiments, a physical stabilization agent is silicon dioxide. In some embodiments, the silicon dioxide can be a colloidal silicon dioxide. Colloidal silicon dioxide is also known as fumed silicon dioxide, silica fume or pyrogenic silica. Such silicon dioxides are commercially available under the trademarks Aerosil® (Evonik industries), Cab-O-Sil® (Cabot Corporation) and Wacker HDK® (Waccker-Chemie GmbH).

In some embodiments, the formulation can include a lipidic thickener. Examples of lipid thickeners include, but are not limited to, Akosoft 36, Geleol, Gelucire, Koliwax, hydrogenated oils, or combinations thereof. In some embodiments, the formulation can include a lipidic thickener in an amount of about 5-25 wt. %, about 10-20 wt. %, about 12-18 wt. %, about 14-16 wt. %, or about 15 wt. % of the total weight of the formulation.

In some embodiments, the formulation can include povidone. Examples of povidone can include different grade povidones such as K30 or K90. In some embodiments, the formulation can include povidone in an amount of about 0.5-10 wt. %, about 1-10 wt. %, about 2-8 wt. %, about 4-6 wt. %, or about 5 wt. % of the total weight of the formulation.

Formulation Formation

In some embodiments, the formulation can be a liquid in the form of a solution. In some embodiments, the formulation is a solution in which the poor permeable molecule (e.g., the API) is suspended in the formulation as a powder. In some embodiments, the formulation can be a water-free reverse microemulsion or a water-free reverse emulsion. In some embodiments, the formulation is homogeneous. A homogeneous formulation can be any single or multiple phase formulation which can be used in the manufacture of a bulk fill formulation in compliance with FDA Guidance for Industry ANDAS: Blend Uniformity dated Aug. 3, 1999, and/or in the manufacture of a viable final pharmaceutical dosage form in compliance with the Content Uniformity Test criteria (excluding mass variation evaluation—European Pharmacopeia Uniformity of Dosage Units 2.9.40, USP General Chapter <905> and Japanese Pharmacopeia 6.02 Uniformity of Dosage units) and/or which can meet the compliance of stable drug substance assay results on stratified samples taken across the manufacturing process.

The formulations disclosed herein can be prepared according to the following processes. The formulation can be a blend of the different excipients. In some embodiments, excipients with the smallest quantities can be added first and the thickener can be added towards the end before the API is added. In some embodiments, the formulation is a clear solution and the API (i.e., poorly permeable molecule or salt thereof) is suspended in this formulation as a powder. The API can be a pure API crystalline, mills, micronized, lyophilized, spray dried or any method know to the person skilled in the art to obtain solid API such as atmospheric spray freeze drying. It can also be API in mixture with solid ingredients to yield a solid API such as glucoside derivative, cellulose derivative, or adsorb on another excipient like mesoporous silica, nanotubes or any materials with adsorption properties or API can be complexed such as but not limited to complexation with ion exchange resin.

The formulations disclosed herein can be digestible. As such, the glycerides can be de-esterified in 2-monoglycerides and free fatty acids by pancreatic lipase in the GI juices. The formulation can release sodium caprate that can act as permeation enhancer to promote absorption of the poorly permeable molecule loaded in the formulation. Pancreatic lipase in the presence of colipase can catalyze the lipolysis (also termed hydrolysis or de-esterification) of emulsified oils to produce fatty acids. The rate of fatty acid generation, and thus a measure of the rate of lipolysis can be followed via continuous titration with a pH-stat as described in U.S. Pat. No. 9,259,389 which is hereby incorporated in its entirety by reference. The extent of digestion after 120 min in a pancreatin solution containing a pancreatin extract having an activity of approximately 8 Tributyrin Units (TBUs) per milligram of dry powder in distilled water at the dosage of 250 mg/ml at 37.5° C.+/−0.5° C. can be such that at least about 1 mmol, about 1.5 mmol, or about 1.7 mmol of the total free fatty acid is released/g of the formulation disclosed herein.

In some embodiments, the extent of digestion after 120 min in CPS models (and thus rate of digestion) is such that at least about 0.2 mmol, about 0.4 mmol, about 0.6 mmol, or about 0.7 mmol of the $C_{10}$ free fatty acid (i.e. capric acid) is released/g of the formulation disclosed herein.

In some embodiments, the formulation disclosed herein is liquid or semi-solid (i.e. possessing a melting temperature range above room temperature) and can be orally administered to a patient in need thereof using pharmaceutical dosage form well known by the one skilled in the art. Such pharmaceutical dosage form can be gelatin or non-gelatin hardshell capsule or softgel capsule. Such capsules can include hard gelatin capsules and soft gelatin capsules and a combination of thereof (e.g., an over encapsulation of a soft gelatin capsule in a hard gelatin capsule or non-gelatin soft and/or hard capsules) This formulation can also be translated into a conventional solid dosage form by the means of techniques well known by one of ordinary skill in the art such as adsorption, hot melt granulation/coating and/or by the mean of selected carriers, diluents, additives and/or binders.

The site of absorption of the poorly permeable molecule can be in the intestine. As such, it is advantageous to co-deliver the formulation and the poor permeable molecule to its site of absorption and where the formulation is digested. In this case, dilution of the formulation in the stomach should be avoided. As a consequence, in some embodiments, the pharmaceutical dosage form is a delayed release dosage form which contains the formulation disclosed herein. Various drug delivery systems can be envisaged by one skilled in the art in order to obtain a delayed release dosage form. Various materials can enable to obtain a delayed release effect. These materials can be used to obtain matrix forms (such as described in CA2439366) or coated forms. Some delayed release and protective results can be obtained using coated dosage forms.

The various type of material which can be used to manufacture a delayed release dosage form are as follow, polymers sensitive to intestinal enzymes such as esterase and lipase (for example Salol, shellac, lipidic compounds (stearic acid, partial glycerides), carnauba wax, hydrogenated castor oil) or protease (for example keratine, gluten, zein), polymers soluble in intestinal pH (this option is the most widely used in the pharmaceutical industry). These polymers can be, polysaccharides as pectin, cellulose or starch derivatives. For example cellulose acetophtalate, hydroxypropyl methylcellulose, cellulose acetohemisuccinate, starch and amylose acetophtalate; vinvlic derivatives (For example, polyvinyl acetate, polyvinyl acetophtalate); acrylic derivatives (For example, Eudragit L, Eudragit FS30D); or maleic acid copolymers.

The delayed release pharmaceutical dosage form can be pH dependent and therefore can use polymers soluble in intestinal pH. In some embodiments, the delayed release pharmaceutical dosage form can be an enteric coated dosage form, in particular an enteric coated capsule as an enteric coated soft gelatin capsule or enteric coated hard-shell capsule, more particularly an enteric coated oval soft gelatin capsule, still more particularly an enteric coated 7.5 oval or smaller soft gelatin capsule. In some embodiments, the gelatin capsule has a hardness of between 8 to 12 N according to the test indicated below, in particular of 9.5N. Smaller dosage form can be even more convenient to deliver the poorly permeable into the intestine. Delayed release dosage form with a size of 3 mm or less can go across the *pylori*'s entrance faster than larger dosage form and then release faster the poor permeable molecule in the intestine after absorption by the patient in that case the dosage for administration may require a dosage form comprised of several small dosage forms swallowed simultaneously.

The manufacture of an enteric coated soft gelatin capsule formulation is well known by one of ordinary skill in the art such as that described in U.S. Pat. No. 9,259,389, which is hereby incorporated by reference in its entirety.

The final delayed release pharmaceutical dosage form can be monolithic or multiparticulate. That means both final dosage form (hardshell capsule, sofigel capsule, or other dosage forms) and intermediate products (pellets, granules . . . ) can be coated. A particular dosage form can be a multiparticulate form (coated pellets filled into hard-shell capsules, granules or pellets used to form several small tablets) in order to minimize inter-individual variability. Examples of plasticizers for the enteric coating which can be associated with the acrylic derivatives (such as Eudragit L) are as follow: glycerol, propylene glycol, sorbitol, sorbitol/sorbitan blends, diethylphatalate, dibutylphtalate, dibutylsebacate, triethylcitrate, triacetin, acetylated monoglyceride 9-45, polyethylene glycol.

Therapeutic Activity

The formulations disclosed herein can have the same therapeutic activity as the poorly permeable molecule or salt thereof which is contained therein. Thus, this disclosure also concerns an enteric pharmaceutical dosage form disclosed herein for use as a drug.

The term "therapeutically effective amount" as used herein can refer to an amount of an agent needed to treat, ameliorate, or prevent the targeted disease condition, or to exhibit a detectable therapeutic or preventative effect. In general, the therapeutically effective dose can be estimated based on the data available for the parenteral administration of the product in humans.

Effective doses of the compounds disclosed herein may be ascertained by conventional methods. The specific dosage level required for any particular patient will depend on a number of factors; including severity of the condition being treated, the general health of the patient (i.e. age, weight and diet), the gender of the patient, the time and frequency of administration, and tolerance/response to therapy. In general, however, the daily dose (whether administered as a single dose or as divided doses) will be in the range 1 to 1000 mg per day, and most usually from 5 to 200 mg per day. Alternatively, dosages can be administered per unit body weight and in this instance a typical dose will be between 0.01 µg/kg and 50 mg/kg, especially between 10 µg/kg and 10 mg/kg, between 50 µg/kg and 2 mg/kg.

Example 1

Example compositions of the formulations disclosed herein can be found in the following Table 2:

TABLE 2

|  | F1 (g) | F1 % w/w | F2 (g) | F2 % w/w | F3 (g) | F3 % w/w | F4 (g) | F4 % w/w |
|---|---|---|---|---|---|---|---|---|
| API | 0.03 | 0.5 | 0.03 | 0.5 | 0.03 | 0.5 | 0.03 | 0.5 |
| Miglyol 812N | 3.18 | 63.55 | 3.24 | 64.7 | — | — | 2.27 | 44.8 |
| Capmul MCM | 1.09 | 21.55 | 1.24 | 24.8 | 1.54 | 29.9 | 1.25 | 24.9 |
| Tween 80 | 0.48 | 9.78 | 0.50 | 10 | — | — | 0.51 | 10 |
| Water | 0.25 | 4.62 | — | — | — | — | — | — |
| Triethyl-citrate | — | — | — | — | 1.00 | 19.8 | 1.00 | 19.8 |
| Kolliphor EL | — | — | — | — | 1.76 | 34.8 | — | — |
| PEG 400 | — | — | — | — | 0.25 | 5 | — | — |
| Propylene Glycol | — | — | — | — | 0.50 | 10 | — | — |
| Total | 5.03 | 100 | 5.01 | 100 | 5.08 | 100 | 5.06 | 100 |

The API in the above formulations was a peptide of five amino acids with a molecular weight around 700 g/mol. In the formulations above, Miglyol, Capmul, and Trielthylcitrate are permeation enhancers, Tween and Kolliphor EL are surfactants to help the kinetic of digestion and then improve the effect of Miglyol and Capmul. Water and PEG 400 and propylene glycol solubilize the API but no activity on permeability. The formulations are designed to act on the poor permeability of the molecules against the intestinal membrane. Chemical and physical instability of the gastrointestinal tract and loss of activity due to acidic conditions in the stomach can be managed by the coating.

The formulations 1-4 (F1-F4) were prepared as described in U.S. Pat. No. 9,259,389 and used a as a comparator to see the enhancement of bioavailability provided by the invention disclosed herein:

Formulation 1 preparation: The amount of API is first dissolved in water, then the Tween 80 is added. The resulting mixture is stirred to obtain a homogeneous solution. Then a solution of Miglyol 812N and Capmul MCM in defined ratio (cf. table 2) is added to the previous mixture. The final emulsion is stirred at room temperature until a homogeneous mixture (no phase separation, API fully solubilized) is obtained. This formulation should be stabilized with silicon dioxide.

Formulation 2 preparation: This formulation encompasses an inventive formulation. Capmul MCM and Miglyol 812N in the selected ratio are mixed together at room temperature. Tween 80 in the defined quantity is then added to the solution. The resulting mixture is homogenized under stirring at room temperature. The API quantity is added at the end and the final mixture is stirred until having a homogeneous suspension (no phase separation, API well dispersed into the fill).

Formulation 3 preparation: This formulation is another solution of the API with a fairly low digestibility but with an alternate permeation enhancer (triethylcitrate). The amount of API is first dissolved in a solution of PEG400 and propylene glycol, then the triethyl citrate and Kolliphor EL are added. The Capmul MCM is added at the end. The resulting mixture is stirred at room temperature to get a homogeneous solution (no phase separation, API fully solubilized).

Formulation 4 preparation: Capmul MCM and Miglyol 812N in the selected ratio are mixed together at room temperature. Tween 80 and triethylcitrate in the defined quantity are then sequentially added to the solution. The resulting mixture is homogenized under stirring at room temperature. The API quantity is added at the end and the final mixture is stirred until a homogeneous suspension (no phase separation, API well dispersed into the fill) is obtained.

Digestibility of Formulations Disclosed Herein

In regard of the digestible ingredient (Miglyol 812N and Capmul MCM) ratio, more than 85%, formulations 1 (reverse emulsion) and 2 (API in suspension) are highly digestible. After 30 min of digestion, formulation 1 release 2.3 mmol of fatty acid per gram of formulation and formulation 2 release 2.1 mmol of fatty acid per gram of formulation. After 3 hours, the maximum quantity of fatty acid release by the formulation 1 and 2 is around 2.8 mmol per gram of formulation, this released quantity is the maximum release possible for all four formulations. More than 75% of fatty acid are released in less than 30 min in these two formulations. Formulation 3 (API in solution) without triglyceride (Miglyol 812N) releases the lowest quantity of fatty acid: 0.6 mmol of fatty acid per gram of formulation after 3 hours of digestion. After 30 min of digestion, only 0.3 (50%) mmol of fatty acid per gram of formulation is released. Formulation 4 releases an intermediate total quantity of fatty acid (2.0 mmol of fatty acid per gram of formulation after 3 hours of digestion) compared to the three others as the level of digestible ingredients is around 70%. 1.7 mmol of fatty acid are released after 30 min corresponding of around 85% of release within 30 min.

The following Table 3 illustrates the bioavailability of a five amino acids peptide of around 700 Da. This peptide was not sensitive to enzymatic degradation and was included into a formulation disclosed herein after administration to dogs.

TABLE 3

| Formulation | 1 | 2 | 3 | 4 |
|---|---|---|---|---|
| AUC average (n = 6) | 17694 | 59321* | 18786 | 32061 |
| Standard deviation | 7317 | 10296 | 15547 | 14439 |
| F (%) | 11 | 37 | 12 | 20 |

*n = 5

A pharmacokinetic study after intraduodenal administration of the formulations in dogs has been performed utilizing non-naive male Beagle dogs (6, 5-10 kg) to determine the bioavailability of the poorly permeable molecule, when delivered in a formulation according to the present invention. To do so, the fill formulation was administered by the mean of an endoscope under anesthesia.

The animals was anesthesied using an intra-muscular injection of Rompun at 0.03 mL/kg followed by an intra-muscular injection of Zoletil 100® at 0.1 mL/kg or any similar drugs.

The test formulation was delivered intraduodenally (at least 4 cm after the pyloric sphincter) using a plastic syringe fitted with a catheter, which is passed through a central canal of an endoscope whereas the animal was placed lying on its left side during the endoscopy. The dosage of poorly permeable molecule to administer was adjusted to each dog body weight recorded on the day of administration, such that each dog received the same dose per kg of animal body weight.

Before each administration and between each animal, the catheter was rinsed with 5 mL of NaCl 0.9% and with at least 20 mL of air. 1 mL blood samples were collected over various time points (usually pre-administration; 0.25, 0.5, 1, 2, 3, 4, 6, 8, 12 hours post-administration) from the Saphenous or cephalic veins of unanesthesised animals, into sodium citrate tubes. Blood plasma was collected after centrifugation of the samples (10 minutes, 3000 g, +4° C.) and stored at −20° C. until analysis.

Pharmacokinetic Study after Intravenous Administration:

The pharmacokinetics of the studied poor permeable molecule has been investigated after intravenous injection in order to calculate its pharmacokinetic parameters & bioavailability after oral or intraduodenal administration.

Dogs were fasted for a period of 14 hours before each intravenous administration and fed 6 hours after administration (during the kinetics measurement). For intravenous administration, the poorly permeable molecule was administered to the dogs, as a single bolus injection into a peripheral vein (Saphenous or cephalic vein) using a plastic syringe.

The dosage of poorly permeable molecule to administer was adjusted to each dog body weight recorded on the day of administration, such that each dog received the same dose per kg of animal body weight. 1 mL blood samples were collected over various time points (usually pre-administration; 0.083, 0.166, 0.25, 0.5, 1, 2, 3, 4, 6, 8, 12 h post-administration) from the Saphenous or cephalic veins of unanesthesised animals, into sodium citrate tubes. Plasma samples were prepared as detailed above (centrifugation and storage at −20° C. until further analysis).

Example 2

Example compositions of the formulations disclosed herein can be found in the following Table 4:

TABLE 4

|  | F5 % w/w | F6 % w/w | F7 % w/w | F8 % w/w |
|---|---|---|---|---|
| API | — | 3.0 | 6.0 | 12.0 |
| Miglyol 812N | 65 | 63.0 | 61.1 | 57.2 |
| Capmul MCM | 25 | 24.3 | 23.5 | 22 |
| Tween 80 | 10 | 9.7 | 9.4 | 8.8 |
| Total | 100 | 100 | 100 | 100 |

The API was an antibody mimetic. Formulation F5 was equivalent to placebo formulation F2. Formulations F6 to F8 were used to test increase of drug load.

Digestibility of formulation disclosed herein:

In placebo formulation (F5), the release of free fatty acids is fast: more than 85% of digestible part of the formulation is digested in less than 30 minutes releasing free fatty acids (mainly C8 and C10 fatty acids) known to increase permeability through the intestinal membrane.

Formulation Manufacture:

Placebo formulation is prepared at room temperature by the addition of the three excipients together in a define ratio (cf. table 4) and mix under magnetic stirring until a single phase solution is achieved (i.e. no phase separation after 24 h without stirring).

The API selected for the Example 2 is a protein of about 12 kDa and more specifically is an antibody mimetic. The lyophilized API was grinded with a mortar and pestle prior its addition into the placebo formulation. The selected amount of API (cf. table 4) corresponding of formulation to be manufacture is added slowly to the placebo solution under continuous stirring. After the addition of the entire quantity of API, the resulting mixture is homogenized with stirring during at least 24 h.

The following Table 5 illustrates the bioavailability of the protein included into a formulation disclosed herein after administration to rats (Formulations 6, 7 and 8) and dogs (Formulation 7).

TABLE 5

|  | Formulation | | | |
|---|---|---|---|---|
|  |  | 7 | | |
|  | 6 | rat | dog | 8 |
| AUC average (n = 4) | 4954 | 9305 | 1863 | 3639 |
| Standard deviation | 6045 | 5109 | 746 | 4022 |
| F (%) | 2.2 | 2.1 | N/A | 0.4 |

The formulations 6, 7, and 8 are administered to the rat via a direct injection in the duodenum procedure. 250 mg of formulation were dosed per rat (Sprague Dawley rats, n=4). This correspond respectively to 25, 50 and 100 mg/kg body weight of antibody. Serum samples were collected at t=, 3, 8, 24, 24, 72, 120 and 168 hours after administration. The concentration of antibody in serum samples was quantified using an antibody specific sandwich ELISA. The average AUC, Standard deviation and bioavailability (F %) are stated in the above table. These values are to be compared to a bioavailability equivalent to zero without any formulation (API in PBS buffer).

A dog study was performed with formulation 7 in four fasted non-naïve male beagle dogs. The dogs were fasted 15-16 hours prior to dose administration and food was returned approximately 1 hour post dose. Each dog received five capsules per day for six consecutive days. The dose was approximately 10 mg/kg antibody animal per day. Serum samples were taken pre-dose on days 1, 2, 3, 4, 5 and 6, 2 h after dosing on days 1, 2, 3, 4, 5 and 6, and 1, 2, 4, 8, 24, 48, 96 and 168 h post dosing on day 6. The concentration of antibody in serum was quantified using an antibody specific sandwich ELISA. The results showed uptake (absorption) of antibody molecule in all four animals with some variation between individuals versus no absorption when the API was simply dissolved in PBS buffer.

Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Reference to "about" a value or parameter herein includes (and describes) variations that are directed to that value or parameter per se. For example, description referring to "about X" includes description of "X". In addition, reference to phrases "less than", "greater than", "at most", "at least", "less than or equal to", "greater than or equal to", or other similar phrases followed by a string of values or parameters is meant to apply the phrase to each value or parameter in the string of values or parameters. For example, a statement that a formulation has at most about 10 wt. %, about 15 wt. %, or about 20 wt. % of a component is meant to mean that the formulation has at most about 10 wt. %, at most about 15 wt. %, or at most about 20 wt. % of a component.

As used herein, the singular forms "a," "an," and "the" are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

This application discloses several numerical ranges in the text. The numerical ranges disclosed inherently support any range or value within the disclosed numerical ranges, including the endpoints, even though a precise range limitation is not stated verbatim in the specification because this disclosure can be practiced throughout the disclosed numerical ranges.

The above description is presented to enable a person skilled in the art to make and use the disclosure, and is provided in the context of a particular application and its requirements. Various modifications to the preferred embodiments will be readily apparent to those skilled in the art, and the generic principles defined herein may be applied to other embodiments and applications without departing from the spirit and scope of the disclosure. Thus, this disclosure is not intended to be limited to the embodiments shown, but is to be accorded the widest scope consistent with the principles and features disclosed herein.

The invention claimed is:

1. A pharmaceutical formulation, comprising:
 a dispersed powder comprising a hydrophilic, synthetic or natural poorly permeable molecule or salt or solvate thereof in an amount 0.01-20 wt. % of the total weight of the formulation, wherein the synthetic or natural poorly permeable molecule is a peptide or protein;
 a lipophilic phase comprising triglycerides of fatty acids in an amount of 50-80 wt. % of the total weight of the formulation;
 at least one hydrophilic surfactant with a hydrophilic lipophilic balance ("HLB") above 10 in an amount of 1-30 wt. % of the total weight of the formulation; and
 at least one lipophilic surfactant comprising partial esters of polyol and fatty acids in an amount of 10-50 wt. % of the total weight of the formulation,
 wherein the pharmaceutical formulation is free of polysaccharides.

2. The formulation of claim 1, wherein the peptide has from 5 to 20 amino acids.

3. The formulation of claim 1, wherein the at least one hydrophilic surfactant is selected from the group consisting of polyoxyethylene (20) monooleate, PEG 8 caprylic/capric glycerides, PEG 6 caprylic/capric glycerides, poly(oxyethylene)(4)Lauryl ether and mixtures thereof.

4. The formulation of claim 1, wherein the triglycerides of fatty acids are medium chain fatty acids.

5. The formulation of claim 1, wherein the lipophilic surfactant comprises a mixture of mono and diglyceride of medium chain fatty acids.

6. The formulation of claim 1, wherein the formulation does not include water.

7. A delayed release pharmaceutical dosage form comprising:
 a pharmaceutical formulation comprising:
  a dispersed powder comprising a hydrophilic, synthetic or natural poorly permeable molecule or salt or solvate thereof in an amount 0.01-20 wt. % of the total weight of the formulation, wherein the synthetic or natural poorly permeable molecule is a peptide or protein;
  a lipophilic phase comprising triglycerides of fatty acids in an amount of 50-80 wt. % of the total weight of the formulation;
  at least one hydrophilic surfactant with a hydrophilic lipophilic balance ("HLB") above 10 in an amount of 1-30 wt. % of the total weight of the formulation; and
  at least one lipophilic surfactant comprising partial esters of polyol and fatty acids in an amount of 10-50 wt. % of the total weight of the formulation, wherein the delayed release dosage form is a coated dosage form whose release is pH dependent,
 wherein the pharmaceutical formulation is free of polysaccharides.

8. A method for treating a patient, comprising administering to a person in need thereof an effective amount of a pharmaceutical formulation comprising:
 a dispersed powder comprising a hydrophilic, synthetic or natural poorly permeable molecule or salt or solvate thereof in an amount 0.01-20 wt. % of the total weight of the formulation, wherein the synthetic or natural poorly permeable molecule is a peptide or protein;
 a lipophilic phase comprising triglycerides of fatty acids in an amount of 50-80 wt. % of the total weight of the formulation;
 at least one hydrophilic surfactant with a hydrophilic lipophilic balance ("HLB") above 10 in an amount of 1-30 wt. % of the total weight of the formulation; and
 at least one lipophilic surfactant comprising partial esters of polyol and fatty acids in an amount of 10-50 wt. % of the total weight of the formulation,
 wherein the pharmaceutical formulation is free of polysaccharides.

9. The method of claim 8, wherein the peptide has from 5 to 20 amino acids.

10. The method of claim 8, wherein the at least one hydrophilic surfactant is selected from the group consisting of polyoxyethylene (20) monooleate, PEG 8 caprylic/capric glycerides, PEG 6 caprylic/capric glycerides, poly(oxyethylene)(4)Lauryl ether and mixtures thereof.

11. The method of claim 8, wherein the triglycerides of fatty acids are medium chain fatty acids.

12. The method of claim 8, wherein the lipophilic surfactant comprises a mixture of mono and diglyceride of medium chain fatty acids.

13. The method of claim 8, wherein the formulation does not include water.

14. The method of claim 8, wherein the pharmaceutical formulation is in a delayed release dosage form comprising a coated dosage form whose release is pH dependent.

* * * * *